(12) United States Patent
Zschunke et al.

(10) Patent No.: US 11,939,288 B2
(45) Date of Patent: *Mar. 26, 2024

(54) PROCESS FOR PRODUCING ALKYL METHACRYLATES WITH IMPROVED WATER AND ACID MANAGEMENT

(71) Applicant: Röhm GmbH, Darmstadt (DE)

(72) Inventors: Florian Zschunke, Frankfurt (DE); Belaid Ait Aissa, Darmstadt (DE); Andreas Rühling, Darmstadt (DE); Gerhard Kölbl, Gernsheim (DE); Steffen Krill, Muehltal (DE); Daniel Helmut König, Stuttgart (DE)

(73) Assignee: Röhm GmbH, Darmstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/058,577

(22) Filed: Nov. 23, 2022

(65) Prior Publication Data

US 2023/0096748 A1 Mar. 30, 2023

Related U.S. Application Data

(63) Continuation of application No. 17/754,076, filed as application No. PCT/EP2020/075679 on Sep. 15, 2020, now Pat. No. 11,560,350.

(30) Foreign Application Priority Data

Sep. 25, 2019 (EP) ..................... 19199483

(51) Int. Cl.
*C07C 67/39* (2006.01)
*C07C 67/54* (2006.01)

(52) U.S. Cl.
CPC .............. *C07C 67/39* (2013.01); *C07C 67/54* (2013.01)

(58) Field of Classification Search
CPC ......... C07C 67/39; C07C 67/54; C07C 69/54; C07C 69/58; G06F 2203/04107; G06F 2203/04112; G06F 3/0412; G06F 3/04164; G06F 3/04182; G06F 3/0443; G06F 3/0446; Y02P 20/582; H10K 59/126; H10K 59/131; H10K 59/40
See application file for complete search history.

(56) References Cited

U.S. PATENT DOCUMENTS

| | | | |
|---|---|---|---|
| 5,969,178 A | 10/1999 | Okamoto et al. | |
| 7,012,039 B2 | 3/2006 | Watanabe et al. | |
| 9,617,199 B2 | 4/2017 | Krill et al. | |
| 9,890,105 B2 | 2/2018 | Krill et al. | |
| 10,301,251 B2 | 5/2019 | Groemping et al. | |
| 10,479,754 B2 | 11/2019 | Krill et al. | |
| 11,124,471 B2 | 9/2021 | Lygin et al. | |
| 2016/0068464 A1 | 3/2016 | Krill et al. | |
| 2016/0251301 A1 | 9/2016 | Krill et al. | |
| 2018/0251418 A1 | 9/2018 | Krill et al. | |
| 2018/0251419 A1* | 9/2018 | Groemping | C07C 45/28 |
| 2021/0032386 A1 | 2/2021 | Krill et al. | |
| 2021/0047259 A1 | 2/2021 | Lygin et al. | |
| 2021/0269385 A1 | 9/2021 | Krill et al. | |

FOREIGN PATENT DOCUMENTS

| | | | |
|---|---|---|---|
| CN | 106588654 | * | 4/2017 |
| KR | 1994-0001849 | | 3/1994 |
| KR | 940001849 | * | 3/1994 |
| WO | 2014/170223 | | 10/2014 |
| WO | 2017/046110 | | 3/2017 |
| WO | 2019/042807 | | 3/2019 |

OTHER PUBLICATIONS

KR940001849 translated (Year: 1994).*
CN106588654 translated (Year: 2017).*
International Search Report dated Nov. 18, 2020, in PCT/EP2020/075679 with English translation, 5 pages.
Written Opinion received dated Nov. 18, 2020, in PCT/EP2020/075679 with English translation, 8 pages.
U.S. Appl. No. 16/637,575, filed Feb. 7, 2020, 2021/0032386, Krill et al.
U.S. Appl. No. 17/250,260, filed Dec. 22, 2020, 2021/0269385, Krill et al.

* cited by examiner

*Primary Examiner* — Yevgeny Valenrod
*Assistant Examiner* — Blaine G Doletski
(74) *Attorney, Agent, or Firm* — Grüneberg and Myers PLLC

(57) ABSTRACT

A process for producing alkyl methacrylates, in particular methyl methacrylate (MMA), includes production of methacrolein (MAL) in a first reaction stage; direct oxidative esterification (DOE) of the methacrolein with an alcohol, preferably methanol, to afford an alkyl methacrylate in a second reaction stage; and workup of the alkyl methacrylate crude product from the second reaction stage. An optimized workup of the reactor output from the oxidative esterification of methacrolein involves minimizing the amount of employed water, the amount of employed acid, and/or the amount of aqueous waste streams, through an optimized recycling of the generated process water streams.

17 Claims, 1 Drawing Sheet

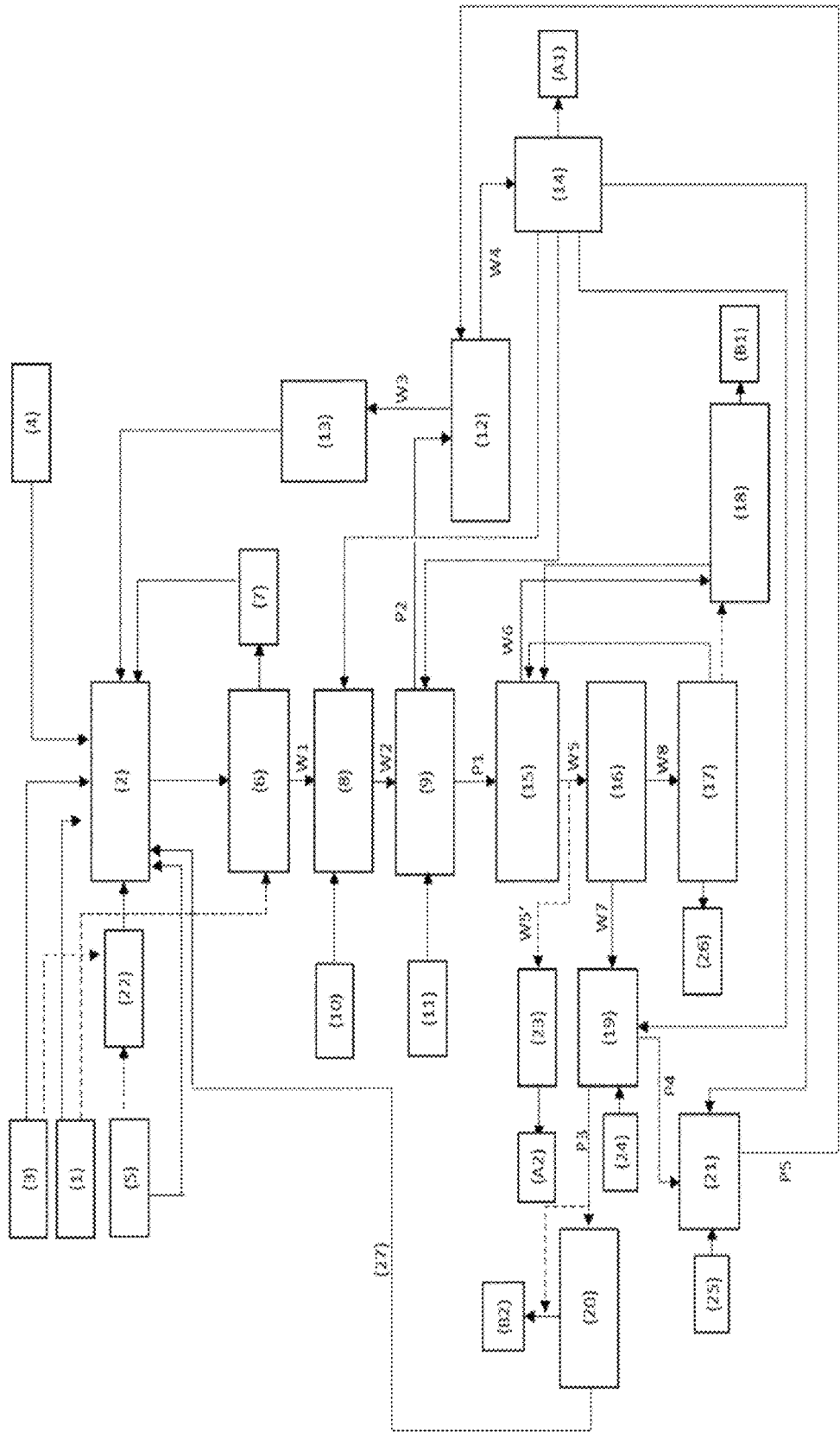

PROCESS FOR PRODUCING ALKYL METHACRYLATES WITH IMPROVED WATER AND ACID MANAGEMENT

CROSS-REFERENCE TO RELATED APPLICATIONS

This application is a continuation of U.S. application Ser. No. 17/754,076, filed on Mar. 23, 2022, which is a National Stage entry under § 371 of International Application No. PCT/EP2020/075679, filed on Sep. 15, 2020, and which claims the benefit of European Application No. 19199483.9, filed on Sep. 25, 2019. The contents of each of these applications is hereby incorporated by reference in its entirety.

BACKGROUND OF THE INVENTION

Field of the Invention

The present invention relates to a process for producing alkyl methacrylates, in particular methyl methacrylate (MMA), comprising production of methacrolein (MAL) in a first reaction stage, direct oxidative esterification (DOE) of the methacrolein with an alcohol, preferably methanol, to afford an alkyl methacrylate in a second reaction stage and workup of the alkyl methacrylate crude product from the second reaction stage.

The present invention especially relates to an optimized workup of the reactor output from the oxidative esterification of methacrolein, wherein the amount of employed water, the amount of employed acid and/or the amount of aqueous waste streams are minimized through an optimized recycling of the generated process water streams.

Description of Related Art

Methyl methacrylate is employed in large amounts to produce polymers and copolymers with other polymerizable compounds. Methyl methacrylate (MMA) is also an important building block for a very wide variety of special esters based on methacrylic acid (MAA) which are producible by esterification of the acid/transesterification of MMA with the corresponding alcohol. There is therefore a great interest in very simple, economic and environmentally friendly production processes for this starting material.

Methyl methacrylate (MMA) is today produced by a very wide variety of processes proceeding from $C_2$-, $C_3$- or $C_4$-building blocks. In one of these processes MMA is obtained by oxidation of isobutylene or tert-butanol with atmospheric oxygen in the gas phase over a heterogeneous contact to afford methacrolein (MAL) and subsequent oxidative esterification reaction of methacrolein using methanol. This process, developed by ASAHI, is described inter alia in documents U.S. Pat. Nos. 5,969,178 and 7,012,039. The very high energy requirements are a particular disadvantage of this process.

The production of MMA according to the so-called Asahi process is carried out starting from C4 (isobutene or tert-butanol) with intermediate isolation of MAL and subsequent direct oxidative esterification ("DOE" for short) of the MAL with methanol to afford MMA and forming methacrylic acid (MAA) as a byproduct by reaction with water.

In a development of the process the methacrolein is obtained from propanal and formalin in the first stage. Such a process is described in WO 2014/170223.

The following scheme 1 shows the reaction matrix for the production of MMA, the production of methacrolein starting from ethylene, synthesis gas and formaldehyde being described by way of example. As explained hereinabove the methacrolein is also obtainable starting from isobutene or tert-butanol.

Scheme 1: Reaction matrix of the C2 process for production of MMA.

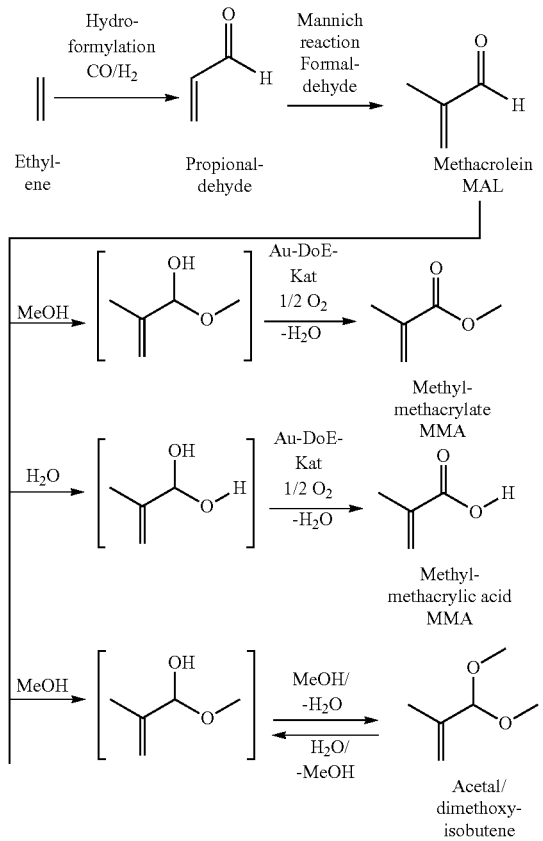

In the oxidative esterification (DOE reaction) methacrylic acid is formed in the presence of water which upon continuous performance of the reaction is typically present in the oxidative esterification reactor in a stationary concentration between 2% and 20% by weight. If the DOE reaction is performed at constant pH the resulting methacrylic acid is at least partially neutralized with alkaline or basic auxiliaries, in the simplest case with alkali compounds.

The crude product from the oxidative esterification typically contains the alkyl methacrylate as the main reaction product, unconverted reactants, in particular methacrolein and alcohol, small amounts of water and various byproducts, such as methacrylic acid (MAA) and salts thereof (for example sodium methacrylate), acetals (for example dimethoxyisobutene DMIB) and also further high-boiling components, for example addition products and Diels-Alder products, for example hydroxyisobutyric acid and corresponding esters thereof, dimeric methacrolein (DIMAL) and esters thereof (DIMAL esters). The high-boiling byproducts must often be removed to obtain the desired alkyl methacrylate product (for example MMA) in a suitable purity for polymerization, typically of markedly greater than 99% by weight.

U.S. Pat. No. 5,969,178 and the prior art referred to therein describes process variants for oxidative conversion of isobutene or tert-butanol into methacrolein and subsequent oxidative esterification to afford MMA. In a first distillation stage a mixture of methacrolein and methanol is removed from the crude product of the oxidative esterification below the top of the column while low-boiling constituents are removed overhead. The MMA-containing bottoms are subsequently passed, together with an unsaturated hydrocarbon, into a second distillation stage in which an azeotrope of methanol and saturated hydrocarbons is removed overhead. The bottoms containing the crude MMA are sent to a further workup while methanol is isolated from the fraction obtained overhead using a phase separator and a third distillation column and recycled into the reactor. It must be taken into account that due to the azeotrope formed the methanol may contain a relatively large amount of water and thus needs to be sent for dewatering.

As an alternative to this process U.S. Pat. No. 5,969,178 discloses workup in only one column wherein the feed must necessarily be located above the column bottom in said column. Low-boiling constituents are removed from the reactor output overhead in this column. A mixture of crude MMA and water which must be sent for further workup remains in the column bottom. A mixture of methacrolein and methanol for recycling into the reactor is finally removed from the column via a side stream. U.S. Pat. No. 5,969,178 indicates that such a process is difficult to perform on account of a wide variety of azeotropes. U.S. Pat. No. 5,969,178 offers no solution for the removal of MMA from methacrylate salt-containing aqueous solutions which are necessarily generated in the described process mode.

U.S. Pat. No. 7,012,039 discloses a slightly different workup of the reactor output from the oxidative esterification. The use of a lead-containing catalyst which obviously also emits lead into the reaction solution renders subsequent workup in particular more complex since insoluble lead salts are formed in the process and require special removal at great cost and complexity. In a first distillation stage methacrolein is distilled off overhead via sieve trays and the aqueous, MMA-containing mixture is passed from the column bottom into a phase separator. In said separator the mixture is adjusted to a pH of about 2 by addition of sulfuric acid. This is followed by separation of the sulfuric acid-containing water from the organic/oil phase by centrifugation. In a further distillation this organic phase is separated into high-boiling constituents and an MMA-containing phase which is withdrawn overhead. The MMA-containing phase is subsequently separated from low-boiling constituents in a third distillation. This is followed by a fourth distillation for final purification.

The problem with the processes according to U.S. Pat. No. 7,012,039 is the sulfuric acid which must be added in large amounts and can have a corrosive effect in parts of the plant. These parts, such as especially the phase separator or else the second distillation column, must therefore be manufactured from materials suitable therefor. No recirculation of acid-containing aqueous streams apparent to a person skilled in the art is derivable from this disclosure. The process according to U.S. Pat. No. 7,012,039 further provides no option for recovery of methacrylic acid or the residual methanol remaining in the product.

WO 2014/170223 describes a similar process to U.S. Pat. No. 7,012,039. It differs in that the pH in the oxidative esterification is adjusted by addition of a methanolic sodium hydroxide solution to a recirculating system. The pH regulation serves, inter alia, to protect the catalyst. Furthermore, removal of the aqueous phase in the phase separation is simpler on account of the salt content. However this also has the result that the methacrylic acid formed is present as the sodium salt and is later removed and discarded with the aqueous phase. In the variant comprising sulfuric acid addition in the phase separation the free acid is recovered but at the cost of generating sodium (hydrogen)sulfate which can lead to other problems upon disposal.

WO 2017/046110 describes a process for producing MMA, wherein the crude product from the oxidative esterification is worked up by distillation of the aqueous phase from an extraction which contains methanol, at least one alkali metal salt, methacrylic acid and a strong inorganic acid. The low-boiling fraction from this distillation stage, which contains mainly methanol, is recycled into the oxidative esterification. The aqueous bottoms fraction is discharged and disposed of A side stream from the distillation containing water and methacrylic acid may be sent to the extraction. Addition of a strong acid during the extraction of the crude product neutralizes salts of methacrylic acid, thus allowing the free methacrylic acid to be obtained conveniently.

WO 2019/042807 describes a process for producing PMMA resins which comprises initially producing the monomer. After the oxidative esterification in a reactor the MMA crude product is subjected to aftertreatment by addition of an organic and/or mineral acid to effect hydrolytic cleavage of the byproduct dimethoxyisobutene.

The disadvantage of the prior art processes for workup of the crude product from the oxidative esterification is that relatively large amounts of acid and water are supplied to the process at various points, thus also generating a relatively large proportion of aqueous waste streams which are contaminated with acid and/or organic components and must be disposed of. The addition of strong acids also necessitates elevated equipment cost and complexity in the corresponding process part, such as especially implementation in corrosion-resistant materials.

SUMMARY OF THE INVENTION

Problem

Having regard to the prior art the problem addressed by the present invention is accordingly that of providing a technically improved process for oxidative esterification of methacrolein which is not beset with the above-described disadvantages of conventional processes. The problem addressed by the present invention is especially that of providing an improved workup of the crude product from the oxidative esterification of methacrolein, wherein the amount of employed water and of employed acid and also the amount of aqueous waste streams can be reduced. The problem addressed is especially that of providing a process operable with the lowest possible disposal cost and complexity, in particular through reduced generation of aqueous and organic constituents and acids in the waste stream.

The process shall also be cost-effective compared to the prior art, for example in respect of the materials to be used in the construction of the plant. The process should also make it possible to achieve the greatest possible yield of alkyl methacrylate and to recover methacrylic byproducts, such as methacrylic acid. The process should in principle make it possible to convert and recycle the greatest possible proportion of byproducts.

Solution to the Problem

It has surprisingly been found that the addition of acid and water and the amount of aqueous wastewater can be minimized through an optimized management of the generated process water streams. It has especially been found that optimized and targeted distribution of the aqueous bottoms from the distillation stage for recovery of the alcohol can achieve savings in employed water and/or employed acid and a reduction in the wastewater stream requiring withdrawal from the process.

The above-described problems are solved according to the invention by a process for producing alkyl methacrylates, wherein in a first reaction stage in a reactor I methacrolein (MAL) is produced and in a second reaction stage in a reactor II this is oxidatively esterified with an alcohol, preferably methanol, in the presence of an oxygen-containing gas and with formation of reaction water in the liquid phase to afford an alkyl methacrylate, preferably to afford methyl methacrylate (MMA), characterized in that
  a. the workup of the reaction mixture from reactor II to afford alkyl methacrylate comprises at least one distillation and at least one extraction;
  b. an aqueous phase containing alcohol and an alkali metal and/or alkaline earth metal salt of a Brønsted acid from the extraction is treated in at least one distillation in a column II (distillation stage II) in such a way that in the bottom of the column II a process water stream (bottoms fraction W4) containing reaction water and alkali metal and/or alkaline earth metal salt of a Brønsted acid is formed, wherein in this process water stream the content of alcohol and alkyl methacrylate is less than 5% by weight based on the total process water stream, and
  c. this process water stream from the bottom of the column II (bottoms fraction W4) is partially discharged from the process and sent for disposal and partially recycled into the workup of the reaction mixture from reactor II.

BRIEF DESCRIPTION OF THE DRAWING

The FIGURE shows an example of a schematic flow diagram of the second step of the process according to the invention for producing alkyl methacrylate.

DETAILED DESCRIPTION OF THE INVENTION

Description of the Invention

In the context of the invention the term stream, phase or fraction containing a reactant, product and/or byproduct of the described process is to be understood as meaning that the recited compounds are to be found in the respective stream, for example the predominant proportion of the reactant, product and/or byproduct may be found in the corresponding stream. Further constituents may in principle be present in addition to the recited compounds. The naming of the constituents often serves to elucidate the respective process step.

It is preferable when the at least one distillation of the process according to the invention, for example the distillation stages I; II, III, and IV described hereinbelow, is performed in distillation columns. The distillation columns are, corresponding to the distillation stage, referred to as I; II, III, IV etc. Typical embodiments of distillation columns are known to those skilled in the art. It is typically possible to employ tray columns, fitted for example with sieve trays, cascade trays, turbogrid trays and/or louvred trays, or packed columns, for example random-packed columns (for example with Raschig Super-Rings from Raschig) or columns having regular packings (for example Mellapak from Sulzer). The distillation stages typically afford at least one high-boiling bottoms fraction and at least one low-boiling tops fraction. The distillation temperature in the different distillation stages is chosen by those skilled in the art according to the distillation pressure, the composition of the mixture to be separated, the number of trays and configuration of the distillation column and also further factors. The distillation temperature is preferably in the range from 20° C. to 120° C.

It is preferable when the alcohol is methanol and the alkyl methacrylate is methyl methacrylate (MMA).

It is preferable when the Brønsted acid (hereinbelow also referred to as acid S) is a strong acid, in particular an acid having a $pK_a$ lower than the $pK_a$ of methacrylic acid. The Brønsted acid preferably has a $pK_a$ of less than 3, particularly preferably less than 2. It is possible to employ strong inorganic acids, such as sulfuric acid or phosphoric acid, or strong organic acids, such as methanesulfonic acid or toluenesulfonic acid. The Brønsted acid is preferably sulfuric acid.

The process according to the invention is preferably operated in continuous or semi-continuous fashion. With the exception of discontinuous discharging of waste streams the process is preferably operated in continuous fashion.

It is preferable when the process water stream from the bottom of the column II is partially recycled into the extraction, wherein this recycled process water stream is contacted with an alkyl methacrylate- and alcohol-containing organic phase (in particular organic phase P1) in the extraction.

It is preferable when the process water stream from the bottom of the column II is the bottoms fraction W4 from the preferred process described hereinbelow.

It is preferable when the process water stream from the bottom of the column II is partially recycled into a reactor III (in particular acetal cleaver III wherein acetals present in stream W1 are cleaved), wherein this recycled process water stream is contacted in reactor III with an alkyl methacrylate- and alcohol-containing organic phase (in particular bottoms fraction W1) which has a content of methacrolein acetal (in particular of dimethoxyisobutene) of less than 3% by weight based on the organic phase.

The extraction is preferably performed in an extraction column and/or in a serially arranged series of at least two mixer-settler apparatuses and the process water stream from the bottom of the column II is added below the top of the extraction column or in the mixer region of a mixer-settler apparatus and water, in particular demineralized water, is optionally added in the top region of the extraction column.

The water supplied to the process according to the invention is in particular demineralized water.

It is preferable when the addition of water and optionally of a Brønsted acid to the extraction is carried out above the addition of the process water stream from the bottom of the column II.

The addition of a Brønsted acid is preferably carried out in reactor III and this addition is chosen such that in continuous operation a pH in the range from 1.5 to 2.5 is established in the process water stream from the bottom of the column II (in particular the bottoms fraction W4).

In a preferred embodiment the addition of a Brønsted acid into the process according to the invention is carried out exclusively via the addition in reactor III. It is also conceivable to perform the acid addition at different points in the process in order to allow more precise adjustment of the different pH values for the different process operations.

The extraction preferably affords an organic phase containing alkyl methacrylate and methacrylic acid and the organic phase from the extraction (in particular the organic phase P1 or the tops fraction W5 from distillation stage III) is separated in a distillation stage IV (column IV) into a bottoms fraction containing alkyl methacrylate (in particular bottoms fraction W8) and a lower-boiling tops fraction (in particular tops fraction W7).

The fraction from the column IV is preferably admixed with water and subsequently separated in a phase separator I into an organic phase (in particular organic phase P3) and into an aqueous phase (in particular aqueous phase P4).

It is preferable when the aqueous phase from the phase separator I (in particular aqueous phase P4) is mixed with at least one Brønsted acid in a reactor IV, wherein ester byproducts present in the aqueous phase from the phase separator I are cleaved and alcohol is recovered and wherein the process water stream from the bottom of the column II is optionally partially passed into the reactor IV.

It is preferable when the product from the reactor IV is completely or partially passed into the column II.

In an alternative embodiment the acetal hydrolysis (DMIB+water→MAL to MeOH) in reactor III and the partial ester hydrolysis carried out in reactor IV may be combined in one reaction vessel.

It is preferable when the aqueous phase from phase separator I is completely or partially passed into the column II.

It is preferable when the reaction mixture from reactor II is separated in a distillation stage I (column I), wherein methacrolein and in part alcohol are removed via the tops fraction and recycled to the reactor II.

It is preferable when methacrolein is completely or partially added to the distillation stage I and passed to the reactor II via the tops fraction from the distillation stage I.

It is preferable when the alcohol is methanol and the alkyl methacrylate is methyl methacrylate. The Brønsted acid is preferably sulfuric acid.

First Reaction Stage (MAL Production)

In a first reaction stage the process according to the invention comprises the production of methacrolein (MAL) in a reactor I. According to the invention the first stage of the process for synthesis of the methacrolein is freely choosable. The first reaction stage of the process may comprise either a first stage synthesis based on tert-butanol or isobutylene or a first stage synthesis based on propanal and formalin.

In the case of production of methacrolein (MAL) based on propanal and formalin there are in principle two suitable process variants which provide methacrolein in a quality that may be employed in the second reaction stage (direct oxidative esterification, DOE reaction). Propanal and formalin may be reacted in a stirred reactor or pumped-circulation reactor at temperatures of 20° C. to 120° C. at pressures of 1 bar to 10 bar. This typically requires reaction times of more than 10 min to achieve sufficient conversions. Propanal and formalin may also be reacted to afford MAL at an average pressure between 10 and 100 bar and at relatively high temperatures between 120° C. and 250° C., the reaction achieving the desired high yields with a reaction time of 2 seconds to 20 seconds.

Processes for producing methacrolein are known to those skilled in the art and described for example in Ullmanns Encyclopedia of Industrial Chemistry, 2012, Wiley-VCH Verlag GmbH, Weinheim (DOI: 10.1002/14356007.a01_149.pub2).

The first reaction stage may also be a process proceeding from C4 raw materials, especially oxidation of tert-butanol and/or isobutene. Isobutene or tert-butanol is typically subjected to gas-phase reaction over a heterogeneous contact with oxygen-containing gases and preferably with steam at temperatures of above 300° C. A multiplicity of subvariants and employable catalyst systems and also insulation options are described in the relevant prior art. An overview thereof may be found for example in "Trends and Future of Monomer-MMA Technologies", K. Nagai & T. Ui, Sumitomo Chemical Co., Ltd., Basic Chemicals Research Laboratory, 2005 (www.sumitomo-chem.co.jp/english/rd/report/theses/docs/20040200_30a.pdf).

It is preferable when the first reaction stage in reactor I is a reaction of propanal with formalin. The first reaction stage may optionally comprise a distillation column for removal of low boilers, such as remaining propanal, and/or of high boilers (for example dimeric methacrolein).

Second Reaction Stage (Direct Oxidative Esterification DOE)

In a second reaction stage the process according to the invention comprises the oxidative esterification (DOE reaction) of the methacrolein with an alcohol, preferably methanol, in a reactor II, to obtain an alkyl methacrylate, preferably methyl methacrylate (MMA).

The direct oxidative esterification (DOE reaction) is preferably performed in the liquid phase at a pressure of 2 to 100 bar, preferably at a pressure in the range from 2 to 50 bar, and a temperature in the range from 10° C. to 200° C. over a heterogeneous catalyst. The heterogeneous catalyst is generally selected from supported, gold-containing nanoparticles having a particle size of less than 20 nm, preferably in the range from 0.2 to 20 nm.

The direct oxidative esterification is typically performed with pH control to ensure optimal activity of the catalyst; the pH is preferably controlled to pH 6-8, particularly preferably to pH 7.

The second reaction stage preferably comprises reaction of methacrolein and an alcohol in the presence of an oxygen-containing gas at moderate temperatures between 20° C. and 150° C. at moderate pressures between 1 and 20 bar in the presence of a heterogeneous particulate noble metal-containing catalyst preferably having a particle size of 1 to 300 µm, wherein larger particles are also employable.

The prior art describes a multiplicity of catalysts for this oxidative esterification of MAL with methanol to afford MMA. U.S. Pat. No. 6,040,472 describes Pd—Pb-containing catalysts on an oxidic support; EP 1 393 800 describes gold-containing catalysts comprising gold particles distributed on a silicon oxide or $TiO_2/SiO_2$ support; EP 2 177 267 and EP 2 210 664 describe nickel-containing catalysts having a shell structure; EP 2 210 664 discloses a catalyst comprising nickel oxide and gold nanoparticles on a support; WO 2017/084969 describes catalyst systems based on two or more mixed oxides as the support which likewise comprise nanoparticulate gold as the active component in addition to cobalt oxide.

The reactor II typically comprises a feed of methacrolein (MAL), a feed of alcohol (in particular methanol), a feed of oxygen and/or air and a feed of a base.

The reactants or a portion of the reactants, in particular base and MeOH, may optionally be mixed in an optional mixer before introduction into the reactor II.

Processes for direct oxidative esterification of methacrolein are known to those skilled in the art. Further details concerning the second reaction stage are described for example in U.S. Pat. Nos. 5,969,178, 7,012,039, WO 2014/170223 und WO 2019/042807.

In a preferred embodiment the workup of the reaction mixture from reactor II comprises the steps of:
i. separating the crude product of the oxidative esterification from reactor II in a distillation stage 1, wherein methacrolein and in part alcohol are removed in the tops fraction and recycled to the reactor II and wherein a bottoms fraction W1 containing alkyl methacrylate, methacrylic acid and/or salts thereof, alcohol and water is obtained;
ii. optionally introducing the bottoms fraction W1 into a reactor III and adding at least one acid S, wherein acetals present in stream W1 are cleaved and wherein a stream W2 is obtained;
iii. extracting the stream W1 or W2 with water and separating into an organic phase P1 containing alkyl methacrylate and methacrylic acid and an aqueous phase P2 containing water, acid S and/or salts thereof, alcohol, methacrylic acid and/or salts thereof;
iv. separating the aqueous phase P2 from the extraction in a distillation stage II to obtain a tops fraction W3 containing mainly alcohol and a bottoms fraction W4 containing water, acid S and/or salts thereof and methacrylic acid and/or salts thereof;
v. separating the organic phase P1 from the extraction in a distillation stage III to obtain a tops fraction W5 containing alkyl methacrylate and a bottoms fraction W6 containing methacrylic acid;
vi. separating the tops fraction W5 from distillation stage III in a distillation stage IV to obtain a tops fraction W7 and a bottoms fraction W8 containing alkyl methacrylate;
vii. mixing the tops fraction W7 from the distillation stage IV with water and separating into an organic phase P3 and an aqueous phase P4 in a phase separator I;
viii. optionally mixing the aqueous phase P4 from phase separator I with at least one acid S in reactor IV, wherein ester byproducts present in P4 are cleaved and alcohol is recovered and wherein an aqueous phase P5 is obtained;
wherein the bottoms fraction W4 from distillation stage II is completely or partially passed into one or more of the process parts selected from reactor III, extraction, phase separator I and reactor IV.

Typically the aqueous phases, for example P2 and P4, are the heavier phase and the organic phases, for example P1 and P3, the lighter phase of the respective separation.

The preferred steps of workup of the reaction mixture from reactor II are more particularly described hereinbelow.

Distillation Stage I (Step i)

The process according to the invention preferably comprises separating the reaction mixture from the oxidative esterification from reactor II in a distillation stage I, in particular in a distillation column I, wherein methacrolein and in part alcohol are removed and recycled to the reactor II and wherein a stream W1 containing alkyl methacrylate, methacrylic acid and/or salts thereof, alcohol and water is obtained.

In a preferred embodiment of the process according to the invention the methacrolein is not or only partially passed directly into the reactor II but rather introduced into the process via the distillation stage I. It is preferable when methacrolein is completely or partially added to the distillation stage I and passed to the reactor II via the low-boiling tops fraction from the distillation stage I.

Reactor III—Acetal Cleaver (Optional Step ii)

The process according to the invention preferably comprises introducing the bottoms fraction W1 from distillation stage I into a reactor III (acetal cleaver) and adding at least one acid S, wherein acetals present in the stream W1 are cleaved and wherein a stream W2 is obtained.

In reactor III the acetal byproduct dimethoxyisobutene (DMIB) is preferably cleaved into methacrolein (MAL) and methanol (MeOH). Acetal cleavage is described for example in WO 2019/042807 and JP 11-302224A. Removal of the acetal byproducts in the optional process step ii) can especially reduce discoloration in descendent products of the alkyl methacrylate, such as polymers and moulding materials.

In addition, salts of methacrylic acid, such as especially alkali metal methacrylates, are typically neutralized to form free methacrylic acid in reactor III.

A mixing of the bottoms fraction W1 with at least one acid S and optionally water is typically carried out in the reactor III. Reactor III may be configured in a manner known to those skilled in the art, for example as a tubular reactor preferably fitted with a static mixer, as a stirred reactor or as a combination thereof.

Reactor III preferably comprises an acid feed I, wherein at least one acid S, preferably sulfuric acid, is supplied. The at least one acid S may also be supplied (exclusively or partially) via the recycling of the bottoms fraction W4 from the distillation stage II. Reactor III may optionally comprise a water feed in addition to the acid feed I.

The pH in the reactor III is preferably in the range from 0 to 7.0, preferably 0.5 to 5.0.

The addition of the at least one acid S (preferably sulfuric acid) into the reactor III is typically chosen such that the aqueous phase P2 in the extraction has a pH in the range of not more than pH 4, preferably pH 1.5 to pH 3.

In a preferred embodiment the optional process step ii) is realized and the addition of acid S (preferably sulfuric acid) in reactor III, especially the addition of the acid S via the acid feed I, is chosen such that in continuous operation a pH in the range from 0 to 3, preferably of 2, is established in the bottoms fraction W4 from distillation stage II.

In a preferred embodiment the optional process step ii) is realized and the addition of fresh acid S (preferably sulfuric acid) into the process according to the invention is carried out exclusively via the feed into reactor III, preferably via the acid feed I.

Extraction (Step iii)

The process according to the invention comprises at least one extraction.

The process preferably comprises extraction of the stream W1 (without optional step ii)) or W2 (with optional step ii)) with water and separation into an organic phase P1 (typically the light phase) containing alkyl methacrylate and methacrylic acid and an aqueous phase P2 (typically the heavy phase) containing water, acid S and/or salts thereof, alcohol, methacrylic acid and/or salts thereof. The addition of water is preferably carried out in the upper part of the column.

The organic phase P1 typically contains mainly the alkyl methacrylate and organic byproducts of the reaction, such as methacrylic acid and further high-boiling byproducts, and smaller amounts of water and methanol. The aqueous phase P2 typically contains little in the way of organic products and contains mainly water and methanol and alkali metal or alkaline earth metal salts from the neutralization and salts of methacrylic acid, in particular alkali metal salts of methacrylic acid.

It is preferable when at least one acid S is added during the extraction. The addition of the at least one acid S (preferably sulfuric acid) in the extraction is preferably chosen such that the aqueous phase P2 in the extraction has a pH in the range of not less than 3. The addition of the acid S in the extraction typically neutralizes salts of methacrylic acid, such as alkali metal methacrylates in particular.

Water may optionally be added to the extraction via an optional feed II. Acid S may optionally be added to the extraction, for example via an optional acid feed and/or together with the water feed II. The water and optionally the acid S may also be supplied to the extraction (exclusively or partially) via the recycling of the bottoms fraction W4 from the distillation stage II.

The extraction in step iii) is preferably performed in an extraction column. Typical embodiments of extraction columns are known to those skilled in the art. Typically employable columns include tray columns or packed columns, for example random-packed columns (for example with Raschig rings) or columns comprising regular packings (for example Mellapak from Sulzer).

In a preferred embodiment the addition of water to the extraction is carried out via the water feed II in the upper region of a distillation column, preferably to the first extraction stage, preferably above any recycling of the bottoms fraction W4 from the distillation stage II.

In a preferred embodiment the extraction (step iii) is performed in an extraction column and the bottoms fraction W4 from distillation stage II is added in the middle region of the extraction column, preferably below the first extraction stage, particularly preferably below the second extraction stage. It is further preferable when the addition of water and optionally acid S to the extraction in the extraction column is carried out above the addition of the bottoms fraction W4 from distillation stage II.

The organic phase P1 from the extraction, which contains the greatest proportion of the desired alkyl methacrylate product, is preferably further purified via the distillation stages III and IV and optionally V and VI described hereinbelow. The organic phase P1 which contains the predominant proportion of the alkyl methacrylate is freed initially of higher-boiling components (distillation stage III) and subsequently of lower-boiling components (distillation stage IV).

The aqueous phase W4 typically contains mineral salts of the corresponding Brønsted acid, wherein the salt content is in the range from 0.5% to 15% by weight based on W4. The recycling of the salt-containing phase W4 into the extraction typically brings about an improvement in extraction performance. In general this effect is based on a density which is elevated compared to DM water and thus a higher density difference compared to the organic phase.

Distillation Stage II—Alcohol Recovery (Step iv)

The process according to the invention preferably comprises separating the aqueous phase P2 from the extraction in a distillation stage II (preferably in a distillation column II) to obtain a low-boiling tops fraction W3 containing mainly alcohol and a high-boiling bottoms fraction W4 containing water, acid S and/or salts thereof and methacrylic acid and/or salts thereof.

It is preferable when the tops fraction W3 is completely or partially recycled into the reactor II.

According to the invention the aqueous bottoms fraction from the distillation stage II is recycled to one or more different points of the process according to the invention, thus saving water and/or acid S and reducing the amount of aqueous waste streams. According to the invention the bottoms fraction W4 from distillation stage II is completely or partially passed into one or more of the process parts selected from reactor III, extraction, phase separator I and reactor IV.

In a preferred embodiment of the process a portion of the bottoms fraction W4 from distillation stage II is continuously and/or discontinuously discharged from the process (as a purge).

The bottoms fraction W4 from distillation stage II is preferably completely or partially recycled into the extraction (step iii). Preferred embodiments of the addition of W4 to the extraction are described hereinabove.

The bottoms fraction W4 from distillation stage II is preferably completely or partially passed into the phase separator I (step vii).

In a preferred embodiment the optional process step ii) (acetal cleaver) is realized and the bottoms fraction W4 from distillation stage II is completely or partially recycled into the reactor III (acetal cleaver).

In a preferred embodiment the optional process step viii) is realized and the bottoms fraction W4 from distillation stage II is completely or partially passed into the reactor IV (ester hydrolysis).

In a preferred embodiment the recycling of the bottoms fraction W4 is carried out into two or more of the recited process parts.

The aqueous bottoms fraction W4 preferably has a pH in the range from 1 to 3, preferably 1.5 to 2.5. The aqueous bottoms fraction W4 preferably contains more than 60% by weight, preferably more than 80% by weight, based on the total weight of W4, of water. The bottoms fraction W4 preferably contains less than 10% by weight, preferably less than 5% by weight, particularly preferably less than 1% by weight, based on the total weight of W4, of alcohol, in particular methanol.

Distillation Stage III—Removal of the High Boilers (Step v)

The process according to the invention preferably comprises the separating of the organic phase P1 from the extraction in a distillation stage III (in particular in a distillation column III) to obtain a low-boiling tops fraction W5 containing alkyl methacrylate and a high-boiling bottoms fraction W6 containing methacrylic acid.

In one embodiment a portion of the tops fraction W5 may be passed into a phase separator II. The aqueous phase may be supplied to reactor IV.

In a preferred embodiment the bottoms fraction W6 containing methacrylic acid may be passed into an optional distillation stage VI (distillation column VI), wherein the amount of alkyl methacrylate in W6 is reduced and the tops fraction from the distillation stage VI containing alkyl methacrylate may be recycled into the distillation stage III.

In a preferred embodiment methacrylic acid may be obtained as a further product from the bottoms fraction W6 and/or from the bottoms fraction from the optional distillation stage VI. Details of this are described for example in WO 2017/046110.

Alternatively, one or more or all distillation stages III, IV and V for purification of the alkyl methacrylate may also be replaced by a crystallization.

Distillation Stage IV—Removal of the Low Boilers (Step vi)

The process according to the invention preferably comprises the separating of low-boiling tops fraction W5 from distillation stage III in a distillation stage IV (in particular in a distillation column IV) to obtain a low-boiling tops fraction W7 and a high-boiling bottoms fraction W8 containing alkyl methacrylate.

The bottoms fraction W8 may preferably be passed into a further optional distillation stage V (in particular distillation column V), wherein a final purification of the alkyl methacrylate is carried out and the alkyl methacrylate as tops fraction from the optional distillation stage V is discharged from the process as product.

The bottoms fraction from the optional distillation stage V may optionally be passed into the distillation stage III and/or the distillation stage VI.

Phase Separator I (Step vii)

The process according to the invention preferably comprises the mixing of the tops fraction W7 from the distillation stage IV with water and separation into an organic phase P3 (typically the light phase) and an aqueous phase P4 (typically the heavy phase) in a phase separator I.

Typical configurations of phase separators are known to those skilled in the art.

From the phase separator I the organic phase P3 may preferably be discharged from the process as an organic waste stream completely or partially, continuously or discontinuously. It is preferable when the organic phase P3 from the phase separator I is completely or partially passed into an optional distillation stage VII (MAL recovery) in which methacrolein is recovered and sent to the oxidative esterification in reactor II.

In an alternative embodiment the aqueous phase P4 from the phase separator I is completely or partially passed into the distillation column II (alcohol recovery). This is carried out in particular if the optional process step viii) has not been realized.

It is also possible to discharge the aqueous phase P4 from phase separator I as an aqueous wastewater stream completely or partially, continuously and/or discontinuously.

The phase separator I preferably comprises a water feed III. The water may also be supplied (exclusively or partially) via the recycling of the bottoms fraction W4 from the distillation stage II.

Reactor IV—Ester Hydrolysis (Optional Step viii)

The process according to the invention preferably comprises mixing the aqueous phase P4 from phase separator I with at least one acid S in reactor IV (ester hydrolysis), wherein ester byproducts present in P4 are cleaved and alcohol is recovered and wherein an aqueous phase P5 is obtained.

In optional reactor IV ester byproducts which have a lower boiling point than methyl methacrylate, in particular saturated esters such as alkyl isobutyrates and alkyl propionates, for example methyl isobutyrate, methyl propionate, are typically hydrolyzed, thus allowing alcohol, preferably methanol, to be recovered.

In a preferred embodiment of the process the optional process step viii) is realized and the aqueous phase P5 from reactor IV (ester hydrolysis) is completely or partially passed into the distillation column II. The alcohol recovered in the ester hydrolysis is typically supplied to the reactor II via the tops fraction W3.

A portion of the aqueous phase P5 from reactor IV may also be continuously and/or discontinuously discharged as an aqueous wastewater stream.

Reactor IV preferably comprises an acid feed IV, wherein at least one acid S, preferably sulfuric acid, is supplied. The at least one acid S may also be supplied (exclusively or partially) via the recycling of the bottoms fraction W4 from the distillation stage II. Reactor IV may optionally comprise a water feed in addition to the acid feed IV.

DESCRIPTION OF THE FIGURE AND LIST OF REFERENCE NUMERALS

The FIGURE shows by way of example a possible schematic flow diagram of the second process step (oxidative esterification of MAL and workup of the product stream) of the process according to the invention for producing alkyl methacrylate. Reactor I of the process according to the invention for MAL synthesis is not shown.

(1) MAL feed into reactor II
(2) Reactor II for oxidative esterification of MAL
(3) Alcohol (in particular methanol) feed into reactor II
(4) Oxygen and/or air feed into reactor II
(5) Base feed into reactor II
(6) Distillation column I for removal of MAL
(7) Low-boiling fraction containing MAL and alcohol for recycling into reactor II (recycling stream)
(8) Reactor III (acetal cleaver) for cleavage of acetal byproducts (for example dimethoxyisobutene (DMIB) to afford MAL and MeOH) (optional)
(9) Extraction
(10) Optional acid feed I to (8)
(11) Optional water feed II to (9)
(12) Distillation column II for recovery of alcohol
(13) Low-boiling fraction from distillation column II containing alcohol for recycling into reactor II
(14) Bottoms fraction from distillation column II containing water, acid and alkylmethacrylic acid and/or salts thereof
(15) Distillation column III for removal of high boilers
(16) Distillation column IV for removal of low boilers
(17) Distillation column V for final purification of MMA
(18) Distillation column VI for reducing the amount of alkyl methacrylate in the bottoms stream from (15) (optional)
(19) Phase separator I for workup of the low-boiling fraction from column IV (16)
(20) Distillation column VII for recovery of MAL from organic phase from phase separator I (19) (optional)
(21) Reactor IV (ester cleaver) for recovery of alcohol from ester byproducts (for example saturated esters such as alkyl isobutyrate, alkyl propionate) (optional)
(22) Apparatus for mixing the reactants mixer I (optional)
(23) Water treatment (optional)
(24) Water feed III to (19) (optional)
(25) Acid feed IV to (21) (optional)
(26) Alkyl methacrylate product stream
(27) Recycling stream containing MAL
(A1)/(A2) Aqueous waste stream
(B1)/(B2) Organic waste stream

EXPERIMENTAL SECTION

Example 1—with Recycling of W4 into the Extraction (9)

The reaction of methacrolein with methanol in the presence of an oxygen-containing gas in the liquid phase to afford methyl methacrylate (MMA) was carried out in reactor II. The reactor output from reactor II had the following composition: MEOH 43.1% by wt, MAL 8.8% by wt, MMA 37.0% by wt, H2O 6.6% by wt, MAL acetal 360 ppm, remainder 4.4% by wt.

The output from reactor II (2) was directly supplied to the extraction (9). The extraction was performed in an extraction column. A partial water feed II (11) to the extraction was carried out. The aqueous phase P2 from the extraction was passed into column II (12). An aqueous wastewater stream A1 was discharged from the bottoms stream from the column II. A partial recycling of the bottoms stream from the column II (W4) to the extraction (9) was carried out.

In the case of experiment 3 the addition of W4 and water was carried out at the top of the extraction column (9). In the case of experiment 4 the addition of W4 was carried out below the top of the extraction column and the addition of water was carried out at the top of the extraction column (9).

The workup of the organic phase from the extraction was carried out using the columns III (15), IV (16) and V (17). In the column V the MMA product stream (26) was withdrawn as the tops fraction.

The feeds into the extraction (9) and the amount of aqueous waste streams are summarized in table 1 below.

TABLE 1

Summary of experiments 1-4

| | Extraction feeds | | | | Content of | |
|---|---|---|---|---|---|---|
| V no. | Water feed II kg/h | W4 kg/h | Wastewater stream A1 kg/h | Product stream MMA kg/h | methanol and MMA in W4 % by wt | pH W4 |
| 1 (Ref) | 24.1 water 0.50 acid | / | 29.2 W4 complete | 15.65 | MEOH 500 ppm MMA 0 | 2 |
| 2 | 0 water 0.19 acid | 24.1 (75% of W4) | 6.5 (25% of W4) | 15.65 | MEOH 500 ppm MMA 0 | 2 |
| 3 | 8.8 water 0.30 acid | 15.3 (50% of W4) | 15.3 (50% of W4) | 15.65 | MEOH 500 ppm MMA 0 | 2 |
| 4 | 8.8 water 0.30 acid (top) | 15.3 (50% of W4) (below top) | 15.3 (50% of W4) | 15.65 | MEOH 500 ppm MMA 0 | 2 |

Example 2—with Recycling of W4 into Reactor III/Acetal Cleaver

The reaction of methacrolein with methanol in the presence of an oxygen-containing gas in the liquid phase to afford methyl methacrylate (MMA) was carried out in reactor II. The reactor output from reactor II had the following composition: MEOH 43.1% by wt, MAL 8.8% by wt, MMA 37.0% by wt, H2O 6.6% by wt, MAL acetal 360 ppm, remainder 4.4% by wt.

The output from reactor II (2) was passed into the reactor III (8) for workup. Reactor III was in the form of a continuously operated stirred tank with a downstream decanter. A partial feed of 96% sulfuric acid (acid S) to reactor III was carried out via acid feed I (10). The output from reactor III was supplied to the extraction (9).

The extraction was performed in an extraction column. A partial water feed II (11) to the extraction was carried out. The aqueous phase P2 from the extraction was passed into column II (12). An aqueous wastewater stream A1 was discharged from the bottoms stream from the column II. A partial recycling of the bottoms stream from the column II (W4) to the reactor III and/or the extraction (9) was carried out.

The workup of the organic phase from the extraction was carried out using the columns III (15), IV (16) and V (17). In the column V the MMA product stream (26) was withdrawn as the tops fraction.

The feeds into reactor III and the extraction are summarized in table 2 below.

TABLE 2

Summary of experiments 5-7

| | Feeds Reactor III | | Feeds Extraction | | | | | Content of | |
|---|---|---|---|---|---|---|---|---|---|
| V no. | Feed I water & acid kg/h | W4 kg/h | Feed II water kg/h | W4 kg/h | Wastewater A1 kg/h | MAL acetal content in W2 ppm | Product stream MMA kg/h | methanol and MMA in W4 % by wt | pH W4 |
| 5 (Ref) | 21.0 water 0.50 acid | / | 3.1 | / | 29.2 (W4 complete) | 14 | 15.65 | MEOH 500 ppm MMA 0 | 2 |
| 6 | 0 Water 0.23 acid | 21.0 Water (69% of W4) | 3.1 | / | 9.6 (31% of W4) | 14 | 15.65 | MEOH 500 ppm MMA 0 | 2 |
| 7 | 0 Water 0.19 acid | 21.0 (69% of W4) | 0 | 3.1 (10% of W4) | 6.5 (21% of W4) | 14 | 15.65 | MEOH 500 ppm MMA 0 | 2 |

Example 3—with Recycling of W4 into Phase Separator I

The experiment was performed as described in example 1. The tops fraction from the column IV was admixed with water via the water feed III (24) and subsequently separated in phase separator I (19) into an organic phase P3 and into an aqueous phase P4. The aqueous phase P4 was recycled into the column II (12).

A partial recycling of the bottoms stream from the column II (W4) to the phase separator I and/or to the extraction was carried out. The feeds into phase separator I and the extraction are summarized in table 3 below.

TABLE 3

Summary of experiments 8-10

| V no. | Feeds Phase separator I | | Feeds Extraction | | Wastewater A1 kg/h | Product stream MMA kg/h | Content of methanol and MMA in W4 % by wt | pH W4 |
| --- | --- | --- | --- | --- | --- | --- | --- | --- |
| | Feed III water kg/h | W4 kg/h | Feed II water and acid kg/h | W4 kg/h | | | | |
| 8 (Ref) | 2.5 | / | 24.1 water 0.5 acid | / | 29.2 (W4 complete) | 15.65 | MEOH 500 ppm MMA 0 | 2 |
| 9 | 0 | 2.5 (9% of W4) | 24.1 water 0.5 acid | / | 26.7 (91% of W4) | 15.65 | MEOH 500 ppm MMA 0 | 2 |
| 10 | 0 | 2.5 (8% of W4) | 0 water 0.19 acid | 24.1 (78% of W4) | 4.0 (14% of W4) | 15.65 | MEOH 500 ppm MMA 0 | 2 |

Example 4—with Recycling of W4 into Reactor IV/Ester Cleaver

The experiment was performed as described in example 3. The phase separator I was provided with water via water feed III (24). The aqueous phase P4 from phase separator I (19) was passed into the reactor IV (ester cleaver) (21) and via acid feed IV mixed with a 96% sulfuric acid (acid S). The aqueous phase P5 from reactor IV was recycled into column II (12).

A partial recycling of the bottoms stream from the column II (W4) to the reactor IV and/or to the extraction was carried out. The feeds into the reactor IV and the extraction are summarized in table 4 below.

TABLE 4

Summary of experiments 11-13

| V no. | Feeds Reactor IV | | Feeds Extraction | | Wastewater A1 kg/h | Product stream MMA kg/h | Content of methanol and MMA in W4 % by wt | pH W4 |
| --- | --- | --- | --- | --- | --- | --- | --- | --- |
| | Feed IV acid kg/h | W4 kg/h | Feed II water and acid kg/h | W4 kg/h | | | | |
| 11 (Ref) | 0.016 | / | 24.1 water 0.5 acid | / | 29.2 (W4 complete) | 15.65 | MEOH 500 ppm MMA 0 | 2 |
| 12 | 0 | 1.4 (5% of W4) | 24.1 water 0.5 acid | / | 29.2 (95% of W4) | 15.65 | MEOH 500 ppm MMA 0 | 2 |
| 13 | 0 | 1.4 (4% of W4) | 0 water 0.19 acid | 24.1 (75% of W4) | 6.5 (21% of W4) | 15.65 | MEOH 500 ppm MMA 0 | 2 |

It has been found that the process mode according to the invention allows savings in water and/or acid feeds and minimization of the aqueous wastewater stream A1 at identical product quality and yield.

The invention claimed is:

1. A process for producing alkyl methacrylates, the process comprising:
producing methacrolein in a first reaction stage in a reactor I, and
oxidatively esterifying the methacrolein with an alcohol in a second reaction stage in a reactor II in the presence of an oxygen-containing gas, to form reaction water in a liquid phase and to afford an alkyl methacrylate,
wherein a workup of a reaction mixture from the reactor II to afford the alkyl methacrylate comprises at least one distillation and at least one extraction;
wherein an aqueous phase containing the alcohol and an alkali metal and/or alkaline earth metal salt of a Brønsted acid from the at least one extraction is treated in at least one second distillation in a column II to form, in a bottom of the column II, a process water stream containing the reaction water and the alkali metal and/or the alkaline earth metal salt of a Brønsted acid, wherein in the process water stream a content of the alcohol and the alkyl methacrylate is less than 5% by weight based on a total process water stream, and
wherein the process water stream from the bottom of the column II is partially discharged from the process and sent for disposal and partially recycled into the workup of the reaction mixture from the reactor II.

2. The process according to claim 1, wherein the process water stream from the bottom of the column II is partially recycled into the at least one extraction, and is contacted with an alkyl methacrylate- and alcohol-containing organic phase in the at least one extraction.

3. The process according to claim 1, wherein the workup of the reaction mixture further comprises a reactor III, wherein the process water stream from the bottom of the column II is partially recycled into the reactor III.

4. The process according to claim 1, wherein the at least one extraction is performed in an extraction column and/or in a serially arranged series of at least two mixer-settler apparatuses, and
wherein the process water stream from the bottom of the column II is added below a top of the extraction column or in a mixer region of a mixer-settler apparatus of the at least two mixer-settler apparatuses, and water is optionally added in the top of the extraction column.

5. The process according to claim 4, wherein the addition of water and optionally, of a Brønsted acid, to the at least one extraction is carried out above the addition of the process water stream from the bottom of the column II.

6. The process according to claim 3, wherein an addition of a Brønsted acid is carried out in the reactor III and the addition is chosen such that in continuous operation a pH in the range from 1.5 to 2.5 is established in the process water stream from the bottom of the column II.

7. The process according to claim 6, wherein the addition of the Brønsted acid is carried out exclusively via the addition in reactor III.

8. The process according to claim 1, wherein the at least one extraction affords an organic phase containing alkyl methacrylate and methacrylic acid and the organic phase from the at least one extraction is separated in a distillation stage IV into a bottoms fraction containing alkyl methacrylate and a lower-boiling tops fraction.

9. The process according to claim 1, wherein the reaction mixture from the reactor II is separated in a distillation stage I, wherein methacrolein and in part alcohol are removed via a tops fraction and recycled to the reactor II.

10. The process according to claim 9, wherein the methacrolein is completely or partially added to the distillation stage I and passed to the reactor II via the tops fraction from the distillation stage I.

11. The process according to claim 1, wherein the alcohol is methanol and the alkyl methacrylate is methyl methacrylate.

12. The process according to claim 6, wherein the Brønsted acid is sulfuric acid.

13. The process according to claim 4, wherein the water optionally added in the top of the extraction column is demineralized water.

14. The process according to claim 1, wherein the workup comprises addition of a Brønsted acid.

15. The process according to claim 1, wherein the workup does not comprise addition of a Brønsted acid.

16. The process according to claim 1, wherein the workup of the reaction mixture further comprise a reactor III, and where the process water stream from the bottom of the column II is partially recycled into the reactor III.

17. The process according to claim 1, wherein the process water stream from the bottom of the column II does not undergo a further workup before being partially recycled into the workup of the reaction mixture from the reactor II.

* * * * *